United States Patent
Murray

(10) Patent No.: US 6,610,627 B2
(45) Date of Patent: Aug. 26, 2003

(54) CATALYST FOR THE PRODUCTION OF OLEFIN POLYMERS

(75) Inventor: Rex Eugene Murray, Charleston, WV (US)

(73) Assignee: Union Carbide Chemicals & Plastics Technology Corporation, Danbury, CT (US)

( * ) Notice: Subject to any disclaimer, the term of this patent is extended or adjusted under 35 U.S.C. 154(b) by 97 days.

(21) Appl. No.: 10/001,381

(22) Filed: Oct. 24, 2001

(65) Prior Publication Data

US 2002/0065379 A1 May 30, 2002

Related U.S. Application Data

(62) Division of application No. 09/456,853, filed on Dec. 8, 1999, now Pat. No. 6,320,005, which is a division of application No. 09/103,620, filed on Jun. 23, 1998, now Pat. No. 6,103,657.
(60) Provisional application No. 60/051,581, filed on Jul. 2, 1997.

(51) Int. Cl.$^7$ ................................................. B01J 31/00
(52) U.S. Cl. ...................... 502/155; 502/152; 502/123; 502/117; 526/160; 526/943
(58) Field of Search ................................. 502/155, 152, 502/123, 117; 526/160, 943

(56) References Cited

U.S. PATENT DOCUMENTS 5,318,935 A  6/1994  Canich et al. ............... 502/117

FOREIGN PATENT DOCUMENTS

| EP | 0320169 A2 |   | 6/1989 |
|----|-----------|---|--------|
| EP | 0349886   |   | 1/1990 |
| EP | 0509233 A2|   | 10/1992 |
| EP | 0803520 A1|   | 4/1997 |
| WO | WO 9212162|   | 7/1992 |
| WO | WO 9623010|   | 8/1996 |
| WO | WO 96/33202| * | 10/1996 |
| WO | WO 9702298|   | 5/1997 |
| WO | WO 9745434|   | 5/1997 |

OTHER PUBLICATIONS

Organometallics 1997, 16 3282–3302 "Synthesis, Structures, Bonding . . . " Bei et al.
Organometallics 1997, 16, 3303–3313 "Neutral and Cationic Zirconium . . . " Tsukahara, et al.
Organometallics 1997, 16, 3314–3323 "Synthesis, Structures, Dynamics, and Olefin . . . " Kim et al.
J. Am. Chem. Soc. 1995, 117, 3008–3021 "Polymerization of α–Olefins and Butadiene . . . " Linden et al.
Angew. Chem. Int. Ed. Engl. 1994 33, No. 1 95–97 "Facile Reduction of a Dialkyl . . . " Brand et al.
Chem. Soc. Dalton Trans 1994 2015–2017 "Functionalizable 5,5,10,10,15,15,20,20 . . . " Solari et al.
J. Am. Chem. Soc. 1993, 115, 8493–8494 "Cationic d$^0$ Metal Alkyls . . . " Uhrhammer et al.
Angew, Chem Int. Ed. Engl. 1994, 33 No. 21 "Tetraaza[14] annulenezirconium(IV) . . . " Giannini, et al.
J. Am. Chem Soc. 1994, 116, 4382–4390 "Synthesis of Molybdenum and Tungsten Complexes That . . . " Kol, et al.
Organometallics 1995, 14, 1827–1833 "[N, N'–Bis(trimethylsilyl)benzamidinato] . . . " Flores, et al.
Inorg. Chem. 1996, 35, 6546–6551 "N–Methyl–2–(methylamino)troponiminate . . . " Dias et al.
Polyhedron vol. 16 No. 3 pp. 541–550, 1997 "Structural Studies of formadine compounds . . . " Cotton et al.
Organometallics 1994, 13, 4398–4405 "Coordination of the Bis(pyridyl)methyl . . . " Gornitzka et al.
Chem. Ber 121, 1403–1406 (1988) "Benzamidinatokomplexe mit Haupt–. . . " Roesky et al.
J. Chem. Soc. Dalton Trans 1995 25–30 "Zirconium Complexes Incorporating . . . " Cloke et al.
Organometallics 1995, 14, 371–386 "Synthesis, Structures, and Reactivity . . . " Tjaden et al.

(List continued on next page.)

Primary Examiner—Ling-Siu Choi

(57) ABSTRACT

A catalyst precursor having the formula:

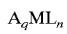

wherein each A has the formula:

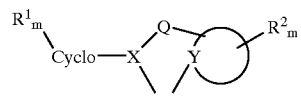

M is a metal selected from the group consisting of Group elements;
  each L is a monovalent, bivalent, or trivalent anion;
  X and Y are each heteroatoms;
  Cyclo is a cyclic moiety;
  each $R^1$ is a group containing 1 to 50 atoms selected from the group consisting of hydrogen and Group 13 to 17 elements, and two or more adjacent $R^1$ groups may be joined to form a cyclic moiety;
  each $R^2$ is a group containing 1 to 50 atoms selected from the group consisting of hydrogen and Group 13 to 17 elements, and two or more adjacent $R^2$ groups may be joined to form a cyclic moiety;
  Q is a bridging group;
  each m is independently an integer from 0 to 5;
  n is an integer from 1 to 4;
  q is 1 or 2;
  and when q is 2, the A groups are optionally connected by a bridging group Z is provided. The catalyst precursor, when combined with an activating cocatalyst, is useful for the polymerization of olefins.

16 Claims, No Drawings

OTHER PUBLICATIONS

J. Chem. Soc. Dalton Trans. 1990 cis– and trans–Dichloro-derivatives . . . Corazza et al. 1335–1344.

Inorg. Chem 1995, 34, 2921–2930, "Oxazoline Early Transition Metal Complexes . . . " Cozzi et al.

Journal of Organometallic Chemistry 503 (1995) 307–314 "Bis–(trimethylsilyl)benzamidinate . . . " Korine et al.

Journal of Organometallic Chemistry 491 (1995) 153–158 " Mono–η–cyclopentadienyl . . ."Gomez et al.

Organometallics 1997, 16, 1247–1252 "Lithium Derivatives of Novel Monoanionic . . . " Deelman et al.

Journal of Organometallic Chemistry 513 (1996) 281–285, "Novel monoanionic di–N,N'–centred chelating . . . " Deelman et al.

J. Chem. Soc., Chem. Commun., 1994 "Transformation of the Bis(trimethylsilyl)methyl into . . . " Hitchcock et al. 2637–2638.

J. Chem. Soc., Chem. Commun. 1994, "Transformation of the Bis(trimethylsilyl)methyl into . . . " Hitchcock et al. 1699–1700.

Inorganica Chimica Acta. 166 (1989) 221–231 "Structural Investigations of the . . . " Clarke, et al.

Fuhrmann et al., Inorg. Chem 1996, 35, 6742–6745.

Derwent Abstract 92–350947/43—Sumitomo Chem Co. Ltd.

Derwent Abstract 89–174462/24—Dow Chemical Co.

Chem. Commun., 1998 849–850 "Novel Olefin Polymerization Catalyst Based on Iron and Cobalt", George J.P. Britovsek et al.

Journal of Organometallic Chemistry 550 (1998) 453–456 "Synthesis and Structural characterisation of aluminum . . . ", Gibson et al.

* cited by examiner

CATALYST FOR THE PRODUCTION OF OLEFIN POLYMERS

CROSS-REFERENCE STATEMENT

This application is a divisional of U.S. application Ser. No. 09/456,853, filed Dec. 8, 1999, now U.S. Pat. No. 6,320,005 now allowed, which is a divisional of U.S. application Ser. No. 09/103,620, filed Jun. 23, 1998, now U.S. Pat. No. 6,103,657, which claims the benefit of provisional U.S. application Ser. No. 60/051,581, filed Jul. 2, 1997, the disclosure of which is incorporated herein by reference.

The invention relates to a family of novel heteroatom-containing catalyst precursors useful for the polymerization of olefins, such as ethylene, higher alpha-olefins, dienes and mixtures thereof.

BACKGROUND

A variety of metallocenes and other single site-like catalysts have been developed to prepare olefin polymers. Metallocenes are organometalic coordination complexes containing one or more π-bonded moieties (i.e., cyclopentadienyl groups) in association with a metal atom. Catalyst compositions containing metallocenes and other single site-like catalysts are highly useful in the preparation of polyolefins, producing relatively homogeneous copolymers at excellent polymerization rates while allowing one to tailor closely the final properties of the polymer as desired.

Recently, work relating to certain nitrogen-containing, single site-like catalyst precursors has been published. PCT Application No. WO 96/23101 relates to di(imine) metal complexes that are transition metal complexes of bidentate ligands selected from the group consisting of:

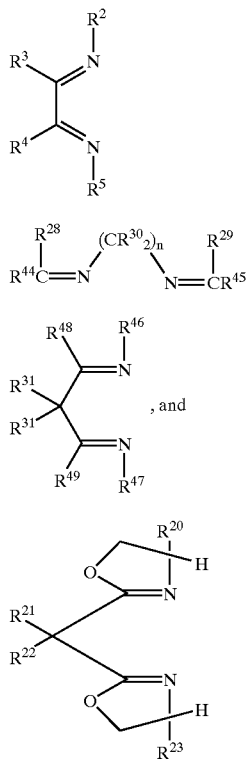

wherein said transition metal is selected from the group consisting of Ti, Zr, Sc, V, Cr, a rare earth metal, Fe, Co, Ni, and Pd;

$R^2$ and $R^5$ are each independently hydrocarbyl or substituted hydrocarbyl, provided that the carbon atom bound to the imino nitrogen atom has at least two carbon atoms bound to it;

$R^3$ and $R^4$ are each independently hydrogen, hydrocarbyl, substituted hydrocarbyl, or $R^3$ and $R^4$ taken together are hydrocarbylene or substituted hydrocarbylene to form a carbocyclic ring;

$R^{44}$ is hydrocarbyl or substituted hydrocarbyl, and $R^{28}$ is hydrogen, hydrocarbyl or substituted hydrocarbyl or $R^{44}$ and $R^{28}$ taken together form a ring;

$R^{45}$ is hydrocarbyl or substituted hydrocarbyl, and $R^{29}$ is hydrogen, substituted hydrocarbyl or hydrocarbyl, or $R^{45}$ and $R^{29}$ taken together form a ring;

each $R^{30}$ is independently hydrogen, substituted hydrocarbyl or hydrocarbyl, or two of $R^{30}$ taken together form a ring;

each $R^{31}$ is independently hydrogen, hydrocarbyl or substituted hydrocarbyl;

$R^{46}$ and $R^{47}$ are each independently hydrocarbyl or substituted hydrocarbyl, provided that the carbon atom bound to the imino nitrogen atom has at least two carbon atoms bound to it;

$R^{48}$ and $R^{49}$ are each independently hydrogen, hydrocarbyl, or substituted hydrocarbyl;

$R^{20}$ and $R^{23}$ are independently hydrocarbyl or substituted hydrocarbyl;

$R^{21}$ and $R^{22}$ are independently hydrogen, hydrocarbyl or substituted hydrocarbyl; and n is 2 or 3;

and provided that:

said transition metal also has bonded to it a ligand that may be displaced by or added to the olefin monomer being polymerized; and when the transition metal is Pd, said bidentate ligand is (V), (VII) or (VIII).

Similarly, PCT Application No. WO 97102298 relates to a process for the polymerization of an olefin, comprising contacting a polymerizable monomer consisting essentially of ethylene, a norbornene or a styrene, with a catalyst system comprising the product of mixing in solution a zerovalent tricoordinate or tetracoordinate nickel compound (II) which has at least one labile ligand, and all ligands are neutral, an acid of the formula HX (IV), and a first compound selected from the group consisting of:

$Ar^1Q_n(III)$; $R^8R^{10}N-CR^4R^5(CR^6R^7)_m-NR^8R^{10}(V)$;

(XVI)

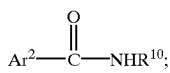

(XVII)

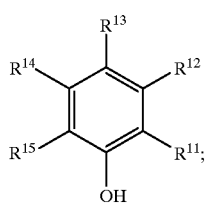

(XVIII)

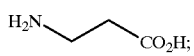

-continued

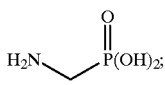 (XIX)

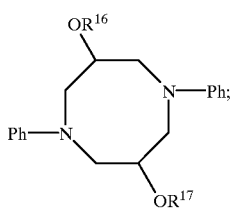 (XX)

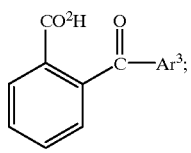 (XXI)

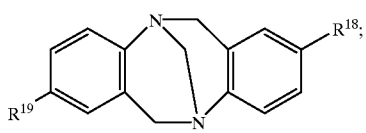 (XXII)

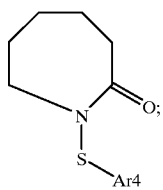 (XXIII)

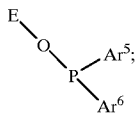 (XXIV)

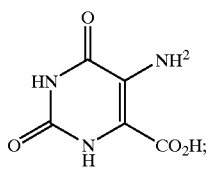 (XXV)

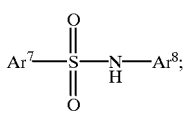 (XXVI)

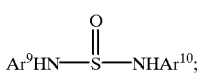 (XXVII)

 (XXVIII)

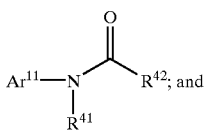 (XXXVI)

-continued

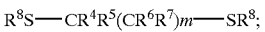 (XXXVII)

wherein:

X is a noncoordinating anion;

$Ar^1$ is an aromatic moiety with n free valencies, or diphenylmethyl;

each Q is $-NR^2R^{43}$ or $-CR^9=NR^3$;

$R^{43}$ is hydrogen or alkyl;

n is 1 or 2;

E is 2-thienyl or 2-furyl;

each $R^2$ is independently hydrogen, benzyl, substituted benzyl, phenyl or substituted phenyl;

each $R^9$ is independently hydrogen or hydrocarbyl; and each $R^3$ is independently a monovalent aromatic moiety;

m is 1, 2 or 3;

each $R^4$, $R^5$, $R^6$, and $R^7$ is independently hydrogen, hydrocarbyl or substituted hydrocarbyl;

each $R^8$ is independently hydrocarbyl or substituted hydrocarbyl containing 2 or more carbon atoms;

each $R^{10}$ is independently hydrogen, hydrocarbyl or substituted hydrocarbyl;

$Ar^2$ is an aryl moiety;

$R^{12}$, $R^{13}$, and $R^{14}$ are each independently hydrogen, hydrocarbyl, substituted hydrocarbyl or an inert functional group;

$R^{11}$ and $R^{15}$ are each independently hydrocarbyl, substituted hydrocarbyl or an inert functional group whose $E_S$ is about −0.4 or less;

each $R^{16}$ and $R^{17}$ is independently hydrogen or acyl containing 1 to 20 carbon atoms;

$Ar^3$ is an aryl moiety;

$R^{18}$ and $R^{19}$ are each independently hydrogen or hydrocarbyl;

$Ar^4$ is an aryl moiety;

$Ar^5$ and $Ar^6$ are each independently hydrocarbyl;

$Ar^7$ and $Ar^8$ are each independently an aryl moiety;

$Ar^9$ and $Ar^{10}$ are each independently an aryl moiety or $-CO_2R^{25}$, wherein $R^{25}$ is alkyl containing 1 to 20 carbon atoms;

$Ar^{11}$ is an aryl moiety;

$R^{41}$ is hydrogen or hydrocarbyl;

$R^{42}$ is hydrocarbyl or $-C(O)-NR^{41}-Ar^{11}$;

$R^{44}$ is aryl;

$R^{22}$ and $R^{23}$ are each independently phenyl groups substituted by one or more alkoxy groups, each alkoxy group containing 1 to 20 carbon atoms; and $R^{24}$ is alkyl containing 1 to 20 carbon atoms, or an aryl moiety.

PCT Application No. WO 96/33202 relates to a transition metal catalyst containing a pyridine or quinoline moiety and having the formula:

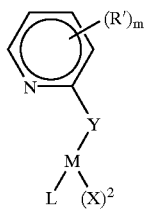

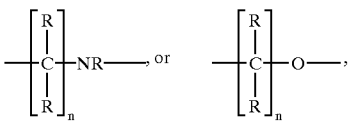

where Y is O, S, NR, each R is independently selected from hydrogen or $C_1$ to $C_6$ alkyl, each R' is independently selected from $C_1$ to $C_6$ alkyl, $C_1$ to $C_6$ alkoxy, $C_6$ to $C_{16}$ aryl, halogen, or $CF_3$, M is titanium, zirconium, or hafnium, each X is independently selected from halogen, $C_1$ to $C_6$ alkyl, $C_1$ to $C_6$ alkoxy, or

L is X, cyclopentadienyl, $C_1$ to $C_6$ alkyl substituted cyclopentadienyl, indenyl, fluorenyl, or

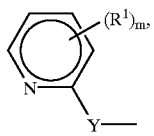

"m" is 0 to 4, and "n" is 1 to 4.

Similarly, Fuhrmann et al., *Inorg. Chem.*, 35:6742–6745 (1996) discloses certain Group 4 metal complexes containing amine, amido, and aminopyridinato ligands such as:

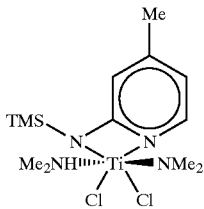

wherein TMS is trimethylsilyl.

An olefin polymerization catalyst composition is described herein having good polymerization activity and productivity. The catalyst composition comprises a heteroatom-containing catalyst precursor having the formula:

$$A_qML_n$$

wherein each A has the formula:

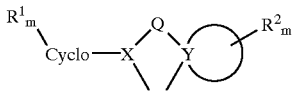

M is a metal selected from the group consisting of Group 3 to 13 elements and Lanthanide series elements;

each L is a monovalent, bivalent, or trivalent anion;

X and Y are each heteroatoms;

Cyclo is a cyclic moiety;

each $R^1$ is independently a group containing 1 to 50 atoms selected from the group consisting of hydrogen and Group 13 to 17 elements, and two or more adjacent $R^1$ groups may be joined to form a cyclic moiety;

each $R^2$ is independently a group containing 1 to 50 atoms selected from the group consisting of hydrogen and Group 13 to 17 elements, and two or more adjacent $R^2$ groups may be joined to form a cyclic moiety;

Q is a bridging group;

each m is independently an integer from 0 to 5;

n is an integer from 1 to 4;

q is 1 or 2;

and when q is 2, the A groups are optionally connected by a bridging group Z.

The catalyst precursor may be conveniently prepared by reacting an organometal compound with a heteroatom-containing ligand of the formula:

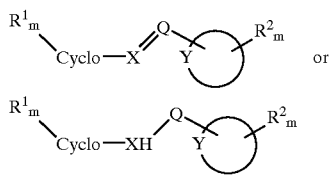

wherein X, Y, Q, Cyclo, $R^1$, $R^2$, and m have the meanings stated above.

SUMMARY OF THE INVENTION

The invention provides a catalyst precursor of the formula:

$$A_qML_n$$

wherein each A has the formula:

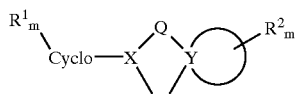

M is a metal selected from the group consisting of Group 3 to 13 elements and Lanthanide series elements;

each L is a monovalent, bivalent, or trivalent anion;

X and Y are each heteroatoms;

Cyclo is a cyclic moiety;

each $R^1$ is independently a group containing 1 to 50 atoms selected from the group consisting of hydrogen and Group 13 to 17 elements, and two or more adjacent $R^1$ groups may be joined to form a cyclic moiety;

each $R^2$ is independently a group containing 1 to 50 atoms selected from the group consisting of hydrogen and Group 13 to 17 elements, and two or more adjacent $R^2$ groups may be joined to form a cyclic moiety;

Q is a bridging group;

each m is independently an integer from 0 to 5;

n is an integer from 1 to 4;

q is 1 or 2;

and when q is 2, the A groups are optionally connected by a bridging group Z; along with a catalyst composition comprising this catalyst precursor and an activating cocatalyst, as well as a process for the polymerization of olefins, using this catalyst composition.

The invention also provides a catalyst precursor comprising the reaction product of an organometal compound and heteroatom-containing ligand having a formula selected from the group consisting of:

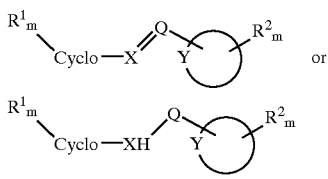

wherein X and Y are each heteroatoms;
Cyclo is a cyclic moiety;
each $R^1$ is a group containing 1 to 50 atoms selected from the group consisting of hydrogen and Group 13 to 17 elements, and two or more adjacent $R^1$ groups may be joined to form a cyclic moiety;
each $R^2$ is a group containing 1 to 50 atoms selected from the group consisting of hydrogen and Group 13 to 17 elements, and two or more adjacent $R^2$ groups may be joined to form a cyclic moiety;
Q is a bridging group; and
each m is independently an integer from 0 to 5; as well as a catalyst composition comprising this catalyst precursor and an activating cocatalyst, and a process for polymerizing olefins using this catalyst composition.

DETAILED DESCRIPTION OF THE INVENTION

The catalyst precursor may have the formula:

$$A_qML_n$$

In the above formula, each A has the formula:

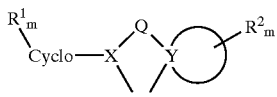

M is a metal selected from the group consisting of Group 3 to 13 and Lanthanide series elements, preferably a Group 4 element, more preferably zirconium.

Each L is a monovalent, bivalent, or trivalent anion, preferably independently selected from the group consisting of halogens; hydrogen; alkyl, aryl, alkenyl, alkylaryl, arylalkyl, hydrocarboxy radicals having 1–50 carbon atoms; amides; phosphides; sulfides; silylalkyls; diketonates; and carboxylates. More preferably, each L is selected from the group consisting of halides, alkyl radicals, and arylalkyl radicals. Most preferably, each L is selected from the group consisting of arylalkyl radicals such as benzyl. Each L may contain one or more heteroatoms.

X and Y are each heteroatoms and are preferably independently selected from the group consisting of N, O, S, and P. More preferably, X and Y are independently selected from the group consisting of N and P. Most preferably, X and Y are both nitrogen.

Y is contained in a heterocyclic ring containing 2 to 7 carbon atoms, preferably 3 to 6 carbon atoms, more preferably 5 carbon atoms. The heterocyclic ring may contain additional heteroatoms (i.e., in addition to Y).

Cyclo is a cylic moiety. Preferably, Cyclo is a carbocyclic ring containing 3 to 7 carbon atoms. More preferably, Cyclo is an aryl group.

Each $R^1$ is independently a group containing 1 to 50 carbon atoms selected from the group consisting of hydrogen and Group 13 to 17 elements, and two or more adjacent $R^1$ groups may be joined to form a cyclic moiety such as an aliphatic or aromatic ring. Preferably, $R^1$ is an alkyl. More preferably, $R^1$ is isopropyl. Optionally, an $R^1$ group may be joined to Q. It is preferred that at least one $R^1$ is ortho to X.

Each $R^2$ is independently a group containing 1 to 50 atoms selected from the group consisting of hydrogen and Group 13 to 17 elements, and two or more adjacent $R^2$ groups may be joined to form a cyclic moiety such as an aliphatic or aromatic ring. Preferably, $R^2$ is hydrogen or an aryl. More preferably, $R^2$ is hydrogen. When $R^2$ is an aryl group and Y is N a quinoline group may be formed. Optionally, an $R^2$ group may be joined to Q.

Q is a bridging group. Preferably, Q contains one or more Group 13, 14, 15, or 16 elements. More preferably, Q contains one or more Group 14 elements. Most preferably, Q is a substituted carbon.

Each m is independently an integer from 0 to 5, preferably 2, and n is an integer from 1 to 4, preferably 3.

The letter q is 1 or 2, and when q is 2 the A groups are optionally connected by a bridging group Z. When present, Z preferably contains one or more Group IIIA, Group IVA, Group VA, or Group VIA elements. More preferably, Z contains one or more Group IVA elements.

In one embodiment of the invention, the catalyst precursor has the formula:

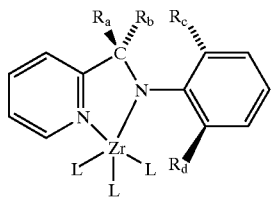

wherein $R_a$ and $R_b$ are each independently selected from the group consisting of alkyl, aryl, heterocyclic groups, and hydrogen; $R_c$ and $R_d$ are each independently selected from the group consisting of alkyl, aryl, and hydrogen; and each L has the meaning stated above.

In another embodiment of the invention, the catalyst precursor has the formula:

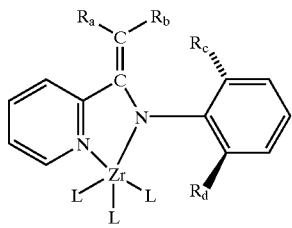

wherein $R_a$, $R_b$, $R_c$, $R_d$, and L have the meanings stated above.

In yet another embodiment of the invention, the catalyst precursor has the formula:

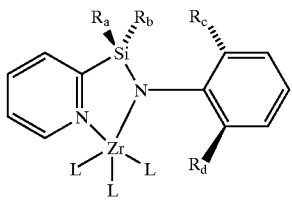

wherein $R_a$, $R_b$, $R_c$, $R_d$, and L have the meanings stated above.

In a further embodiment of the invention, the catalyst precursor has the formula:

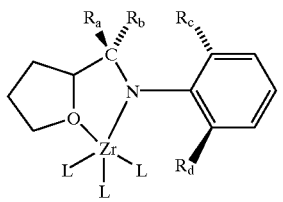

wherein $R_a$, $R_b$, $R_c$, $R_d$, and L have the meanings stated above.

In a particularly preferred embodiment of the invention, the catalyst precursor has the formula:

Compound 1

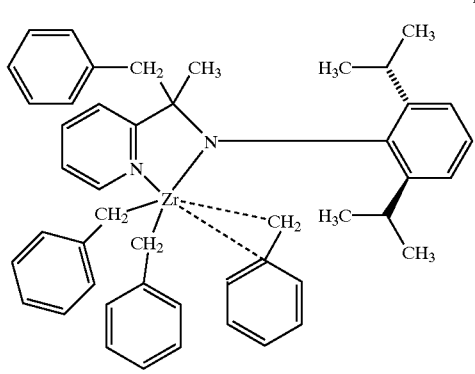

In another particularly preferred embodiment of the invention, the catalyst precursor has the formula:

Compound 2

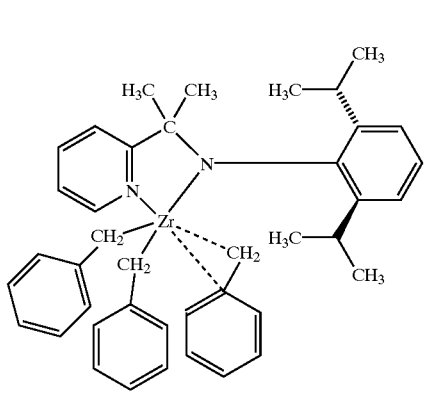

In further particularly preferred embodiment of the invention, the catalyst precursor has the formula:

Compound 3

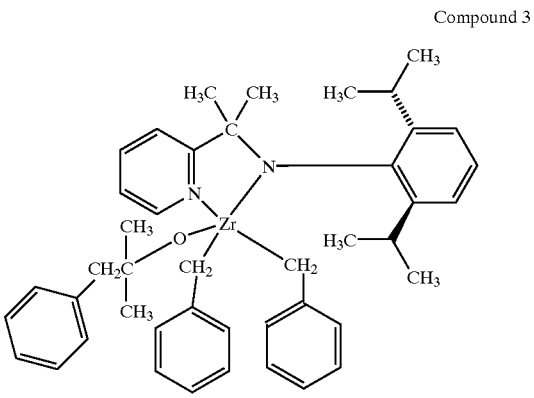

Yet another preferred catalyst precursor is:

Compound 4

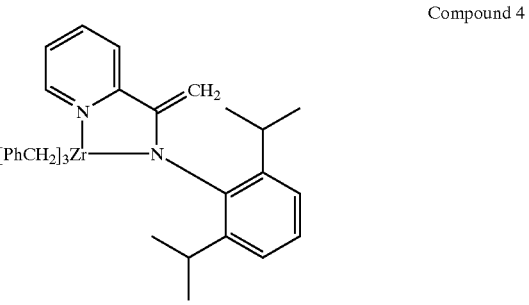

The catalyst precursor may be made by any method. The method of making the catalyst precursor is not critical to the invention. However, one useful method of making the catalyst precursor is by reacting an organometal compound or a metal halide with a heteroatom-containing ligand having a formula selected from the group consisting of:

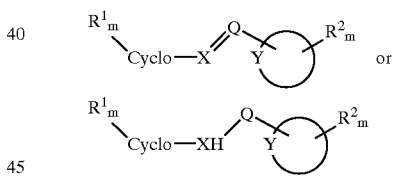

wherein X, Y, Q, Cyclo, $R^1$, $R^2$, and m have the meanings stated above.

Preferably, the catalyst precursor is made by reacting an organometal compound with the heteroatom-containing ligand. Accordingly, in one embodiment of the invention, the catalyst precursor comprises the reaction product of an organometal compound and a heteroatom-containing ligand having a formula selected from the group consisting of:

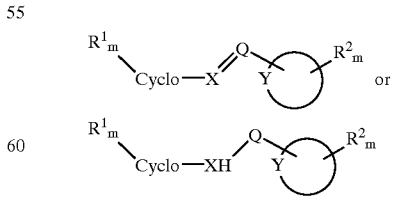

wherein X, Y, Q, Cyclo, $R^1$, $R^2$, and m have the meanings stated above.

The metal of the organometal compound may be selected from Group 3 to 13 elements and Lanthanide series elements. Preferably, the metal is a Group 4 element. More preferably the metal is zirconium.

The organometal compound for example may be a metal hydrocarbyl such as a metal alkyl, metal aryl, or metal arylalkyl. Metal silylalkyls, metal amides, or metal phosphides may also be used. Preferably, the organometal compound is a zirconium hydrocarbyl. More preferably, the organometal compound is a zirconium arylalkyl. Most preferably, the organometal compound is tetrabenzylzirconium.

Examples of useful organometal compounds are tetramethylzirconium, tetraethylzirconium, tetrakis[trimethylsilylmethyl]zirconium, tetrakis[dimethylamino]zirconium, dichlorodibenzylzirconium, chlorotribenzylzirconium, trichlorobenzylzirconium, bis[dimethylamino]bis[benzyl]zirconium, and tetrabenzylzirconium.

Tetramethyltitanium, tetraethyltitanium, tetrakis[trimethylsilylmethyl]titanium, tetrakis[dimethylamino]titanium, dichlorodibenzyltitanium, chlorotribenzyltitanium, trichlorobenzyltitanium, bis[dimethylamino]bis[benzyl]titanium, and tetrabenzyltitanium.

Tetramethylhafnium, tetraethylhafnium, tetrakis[trimethylsilylmethyl]hafnium, tetrakis[dimethylamino]hafnium, dichlorodibenzylhafnium, chlorotribenzylhafnium, trichlorobenzylhafnium, bis[dimethylamino]bis[benzyl]hafnium, and tetrabenzylhafnium.

Tetrakis[tertbutyl]lanthanates; lithiumhexamethyllanthanates; tetrakis[allyl]lanthanates; and tris[bis[trimethylsilyl]methyl]lanthanides.

Because organometal compounds containing lanthanides and some transition metals are often difficult to prepare, it is preferred to prepare catalyst precursors containing these in a two-step process by first reacting the heteroatom-containing ligand with a lithium alkyl to make a lithium amide, and then reacting with a lanthanide or transition metal halide to generate the amide complex.

The heteroatom-containing ligand has the formula:

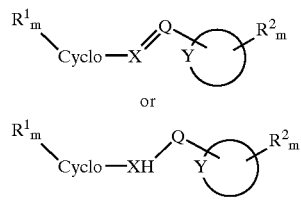

or

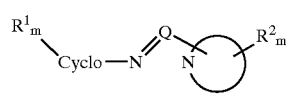

wherein X, Y, Q, Cyclo, $R^1$, $R^2$, and m have the meanings stated above.

Preferably, the heteroatom-containing ligand has the formula:

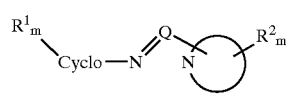

More preferably, the heteroatom-containing ligand is a pyridine/imine ligand of the formula:

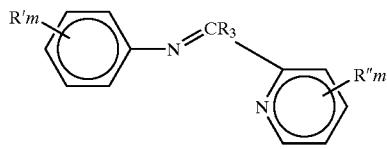

wherein each R' is a hydrocarbon group containing 1 to 20 carbon atoms and two or more adjacent R' groups may be joined to form an aliphatic or aromatic ring;

each R" is a hydrocarbon group containing 1 to 20 carbon atoms and two or more adjacent R" groups may be joined to form an aliphatic or aromatic ring; and $R^3$ is hydrogen, a hydrocarbon group containing 1 to 20 carbon atoms optionally substituted with one or more heteroatoms, or a heteroatom optionally substituted with a hydrocarbon group.

For example, Compound 1 may be made by reacting a substituted pyridine/imine ligand with a zirconium aryl such as tetrabenzyl zirconium:

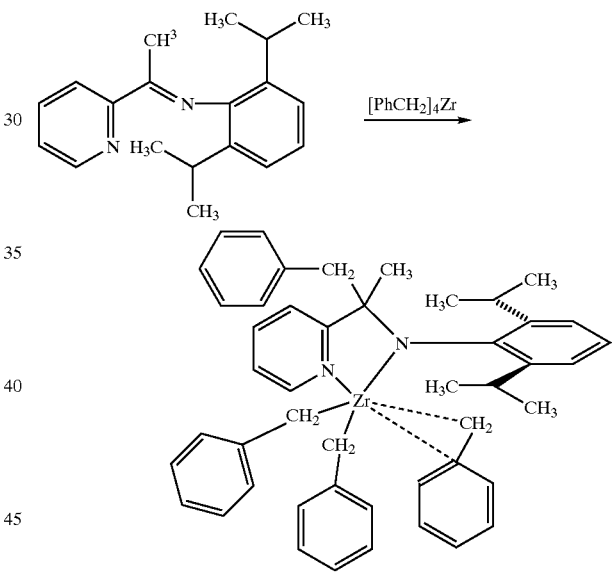

This reaction is preferably carried out in a suitable solvent such as toluene or benzene at a temperature in the range of −50 to 50° C. and a pressure ranging from a vacuum to 1000 psi.

Alternatively and preferably, the catalyst precursor can be made by reacting the heteroatom-containing ligand with a metal halide and then further reacting the product thereof with a Grignard reagent, such as an organomagnesium halide. For instance, the same catalyst precursor, Compound 1, may be made by reacting a substituted pyridine/imine ligand with a zirconium halide such as zirconium tetrachloride, and then further reacting the product thereof with $PhCH_2MgCl$.

Another preferred catalyst precursor, Compound 2, may be made by reacting a substituted pyridine/amine ligand with a zirconium aryl such as tetrabenzyl zirconium:

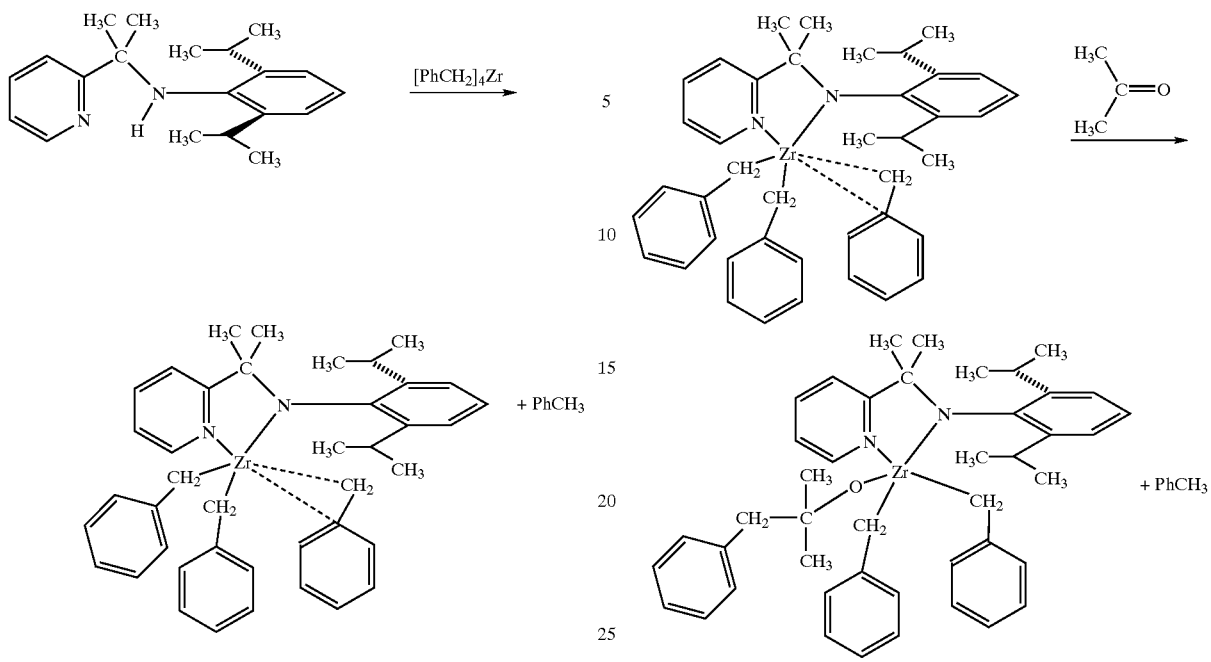

This reaction is preferably carried out in a suitable solvent such as toluene or benzene at a temperature in the range of −50 to 50° C. and a pressure ranging from a vacuum to 1000 psi.

Another preferred catalyst precursor, Compound 3, may be made by reacting Compound 2 with acetone:

As another example, Compound 4 may be made in a multistep procedure by reacting a substituted pyridine/amine ligand sequentially with methyl lithium, chlorotrimethylsilane, zirconium tetrachloride, and benzyl magnesium chloride as follows:

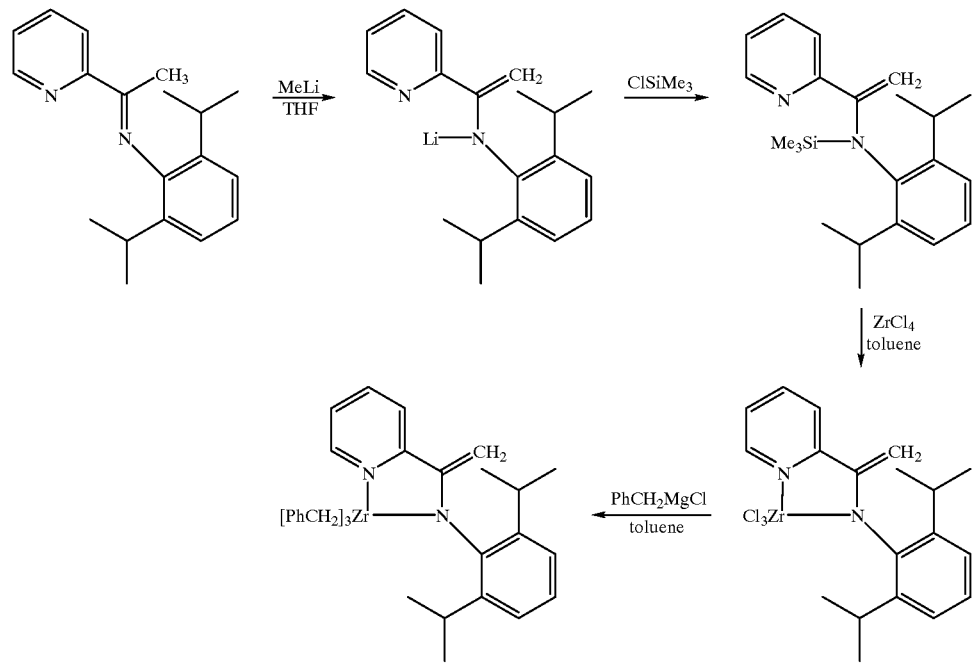

This reaction is preferably carried out in a suitable solvent such as toluene or benzene at a temperature in the range of −50 to 50° C. and a pressure ranging from a vacuum to 1000 psi.

The catalyst precursor may be isolated by conventional methods.

The catalyst composition comprises the catalyst precursor and an activating cocatalyst. The activating cocatalyst is capable of activating the catalyst precursor. Preferably, the activating cocatalyst is one of the following: (a) branched or cyclic oligomeric poly(hydrocarbylaluminum oxide)s which contain repeating units of the general formula —(Al(R*)O)—, where R* is hydrogen, an alkyl radical containing from 1 to about 12 carbon atoms, or an aryl radical such as a substituted or unsubstituted phenyl or naphthyl group; (b) ionic salts of the general formula [A+][BR$_4^-$], where A+ is a cationic Lewis or Bronsted acid capable of abstracting an alkyl, halogen, or hydrogen from the metallocene catalysts, B is boron, and R is a substituted aromatic hydrocarbon, preferably a perfluorophenyl radical; (c) boron alkyls of the general formula BR$_3$, where R is as defined above; or mixtures thereof. The activating cocatalyst may also be an organoaluminum compound, such as tri-isobutylaluminum or diethylaluminum chloride.

Preferably, the activating cocatalyst is a branched or cyclic oligomeric poly(hydrocarbylaluminum oxide) or a boron alkyl. More preferably, the activating cocatalyst is an aluminoxane such as methylaluminoxane (MAO) or modified methylaluminoxane (MMAO), or a boron alkyl.

Aluminoxanes are well known in the art and comprise oligomeric linear alkyl aluminoxanes represented by the formula:

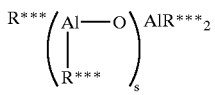

and oligomeric cyclic alkyl aluminoxanes of the formula:

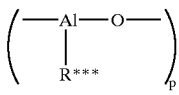

wherein s is 1–40, preferably 10–20; p is 3–40, preferably 3–20; and R*** is an alkyl group containing 1 to 12 carbon atoms, preferably methyl.

Aluminoxanes may be prepared in a variety of ways. Generally, a mixture of linear and cyclic aluminoxanes is obtained in the preparation of aluminoxanes from, for example, trimethylaluminum and water. For example, an aluminum alkyl may be treated with water in the form of a moist solvent. Alternatively, an aluminum alkyl, such as trimethylaluminum, may be contacted with a hydrated salt, such as hydrated ferrous sulfate. The latter method comprises treating a dilute solution of trimethylaluminum in, for example, toluene with a suspension of ferrous sulfate heptahydrate. It is also possible to form methylaluminoxanes by the reaction of a tetraalkyl-dialuminoxane containing $C_2$ or higher alkyl groups with an amount of trimethylaluminum that is less than a stoichiometric excess. The synthesis of methylaluminoxanes may also be achieved by the reaction of a trialkyl aluminum compound or a tetraalkyldialuminoxane containing $C_2$ or higher alkyl groups with water to form a polyalkyl aluminoxane, which is then reacted with trimethylaluminum. Further modified methylaluminoxanes, which contain both methyl groups and higher alkyl groups, i.e., isobutyl groups, may be synthesized by the reaction of a polyalkyl aluminoxane containing $C_2$ or higher alkyl groups with trimethylaluminum and then with water as disclosed in, for example, U.S. Pat. No. 5,041,584.

When the activating cocatalyst is a branched or cyclic oligomeric poly(hydrocarbylaluminum oxide), the mole ratio of aluminum atoms contained in the poly(hydrocarbylaluminum oxide) to total metal atoms contained in the catalyst precursor is generally in the range of from about 2:1 to about 100,000:1, preferably in the range of from about 10:1 to about 10,000:1, and most preferably in the range of from about 50:1 to about 2,000:1. When the activating cocatalyst is an ionic salt of the formula [A+][RR$_4^-$] or a boron alkyl of the formula BR$_3$, the mole ratio of boron atoms contained in the ionic salt or the boron alkyl to total metal atoms contained in the catalyst precursor is generally in the range of from about 0.5:1 to about 10:1, preferably in the range of from about 1:1 to about 5:1.

The catalyst precursor, the activating cocatalyst, or the entire catalyst composition may be impregnated onto a solid, inert support, in liquid form such as a solution, dispersion or neat liquid, spray dried, in the form of a prepolymer, or formed in-situ during polymerization. Particularly preferred among these is a catalyst composition that is spray dried as described in European Patent Application No 0 668 295 A1 or in liquid form as described in U.S. Pat. No. 5,317,036.

In the case of a supported catalyst composition, the catalyst composition may be impregnated in or deposited on the surface of an inert substrate such as silica, carbon black, polyethylene, polycarbonate porous crosslinked polystyrene, porous crosslinked polypropylene, alumina, thoria, zirconia, or magnesium halide (e.g., magnesium dichloride), such that the catalyst composition is between 0.1 and 90 percent by weight of the total weight of the catalyst composition and the support.

The catalyst composition may be used for the polymerization of olefins by any suspension, solution, slurry, or gas phase process, using known equipment and reaction conditions, and is not limited to any specific type of reaction system. Generally, olefin polymerization temperatures range from about 0° C. to about 200° C. at atmospheric, subatmospheric, or superatmospheric pressures. Slurry or solution polymerization processes may utilize subatmospheric or superatmospheric pressures and temperatures in the range of about 40° C. to about 110° C. A useful liquid phase polymerization reaction system is described in U.S. Pat. 3,324,095. Liquid phase reaction systems generally comprise a reactor vessel to which olefin monomer and catalyst composition are added, and which contains a liquid reaction medium for dissolving or suspending the polyolefin. The liquid reaction medium may consist of the bulk liquid monomer or an inert liquid hydrocarbon that is nonreactive under the polymerization conditions employed. Although such an inert liquid hydrocarbon need not function as a solvent for the catalyst composition or the polymer obtained by the process, it usually serves as solvent for the monomers employed in the polymerization. Among the inert liquid hydrocarbons suitable for this purpose are isopentane, hexane, cyclohexane, heptane, benzene, toluene, and the like. Reactive contact between the olefin monomer and the catalyst composition should be maintained by constant stirring or agitation. The reaction medium containing the olefin polymer product and unreacted olefin monomer is withdrawn from the reactor continuously. The olefin polymer product is separated, and the unreacted olefin monomer and liquid reaction medium are recycled into the reactor.

Preferably, gas phase polymerization is employed, with superatmospheric pressures in the range of 1 to 1000 psi, preferably 50 to 400 psi, most preferably 100 to 300 psi, and temperatures in the range of 30 to 130° C., preferably 65 to 110° C. Stirred or fluidized bed gas phase reaction systems are particularly useful. Generally, a conventional gas phase, fluidized bed process is conducted by passing a stream containing one or more olefin monomers continuously through a fluidized bed reactor under reaction conditions and in the presence of catalyst composition at a velocity sufficient to maintain a bed of solid particles in a suspended condition. A stream containing unreacted monomer is withdrawn from the reactor continuously, compressed, cooled, optionally fully or partially condensed as disclosed in U.S. Pat. Nos. 4,528,790 and 5,462,999, and recycled to the reactor. Product is withdrawn from the reactor and make-up monomer is added to the recycle stream. As desired for temperature control of the system, any gas inert to the catalyst composition and reactants may also be present in the gas stream. In addition, a fluidization aid such as carbon black, silica, clay, or talc may be used, as disclosed in U.S. Pat. No. 4,994,534.

Polymerization may be carried out in a single reactor or in two or more reactors in series, and is conducted substantially in the absence of catalyst poisons. Organometallic compounds may be employed as scavenging agents for poisons to increase the catalyst activity. Examples of scavenging agents are metal alkyls, preferably aluminum alkyls, most preferably triisobutylaluminum.

Conventional adjuvants may be included in the process, provided they do not interfere with the operation of the catalyst composition in forming the desired polyolefin. Hydrogen or a metal or non-metal hydride, e.g., a silyl hydride, may be used as a chain transfer agent in the process. Hydrogen may be used in amounts up to about 10 moles of hydrogen per mole of total monomer feed.

Olefin polymers that may be produced according to the invention include, but are not limited to, ethylene homopolymers, homopolymers of linear or branched higher alpha-olefins containing 3 to about 20 carbon atoms, and interpolymers of ethylene and such higher alpha-olefins, with densities ranging from about 0.86 to about 0.96. Suitable higher alpha-olefins include, for example, propylene, 1-butene, 1-pentene, 1-hexene, 4-methyl-1-pentene, 1-octene, and 3,5,5-trimethyl-1-hexene. Olefin polymers according to the invention may also be based on or contain conjugated or non-conjugated dienes, such as linear, branched, or cyclic hydrocarbon dienes having from about 4 to about 20, preferably 4 to 12, carbon atoms. Preferred dienes include 1,4-pentadiene, 1,5-hexadiene, 5-vinyl-2-norbornene, 1,7-octadiene, vinyl cyclohexene, dicyclopentadiene, butadiene, isobutylene, isoprene, ethylidene norbornene and the like. Aromatic compounds having vinyl unsaturation such as styrene and substituted styrenes, and polar vinyl monomers such as acrylonitrile, maleic acid esters, vinyl acetate, acrylate esters, methacrylate esters, vinyl trialkyl silanes and the like may be polymerized according to the invention as well. Specific olefin polymers that may be made according to the invention include, for example, polyethylene, polypropylene, ethylene/propylene rubbers (EPR's), ethylene/propylene/diene terpolymers (EPDM's), polybutadiene, polyisoprene and the like.

The following examples further illustrate the invention.

EXAMPLES

Glossary

Activity is measured in g polyethylene/mmol metal. hr. 100 psi ethylene.

I2 is melt index (dg/min), measured using ASTM D-1238 Condition E at 190° C.

I21 is flow index (dg/min), measured using ASTM D-1238-Condition F.

MFR is Melt Flow Ratio, I21/I2.

BBF is Butyl Branching Frequency, number of butyl branches per 1000 main chain carbon atoms based on infrared measurement techniques.

$M_n$ is Number Average Molecular Weight, as determined by gel permeation chromatography using crosslinked polystyrene columns; pore size sequence: 1 column less than 1000 Å, 3 columns of mixed $5\times10^7$ Å; 1,2,4-trichlorobenzene solvent at 140° C. with refractive index detection.

PDI is Polydispersity Index, equivalent to Molecular Weight Distribution ($M_w/M_n$).

Example 1

Preparation of 2-Acetylpyridine [2,6-Diisopropylphenylimine]Ligand

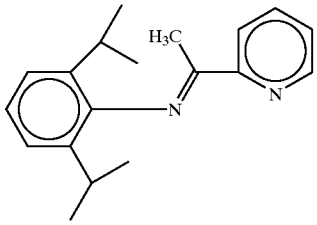

Into a 50 mL round bottom flask equipped with a stir bar and septa was charged 11.0 mmol 2,6-diisopropylaniline and 9.5 mmol 2-acetylpyridine. With vigorous stirring, 0.5 mmol 2-acetylpyridine-HCl was added. The reaction vessel was placed under a strong nitrogen purge and was vented to a trap. The reaction was heated to 160° C. for 2 hours. The reaction vessel was allowed to cool to room temperature. 10 mL hexane was added and stirred vigorously, then allowed to settle overnight. The mixture was filtered and the filtrate was vacuum stripped to obtain the yellow solid product with a melting point of 68–70° C.

Example 2

Preparation of [2-Pyridyl(Me)(PhCH$_2$)C(N-2,6-Diisopropylphenyl)]Zr(PhCH$_2$)$_3$ In a darkened dry box in a darkened room 0.5 mmol (0.14 g) of the ligand of Example 1 was charged to an oven-dried 50 mL round-bottom flask equipped with a stir bar and containing 0.5 mmol (0.23 g) tetrabenzyl zirconium. With vigorous stirring, 7.5 mL benzene-d$_6$ was added to prepare a 0.067M solution. The reaction vessel was immediately covered with foil and the solution was allowed to stir in the dry box overnight.

Example 3

Preparation of [2-Pyridyl(Me)(PhCH$_2$)C(N-2,6-Diisopropylphenyl)]Zr(PhCH$_2$)$_3$ In a dry box, 50 mmol (11.65 g) ZrCl$_4$ was charged to a 300 mL Schlenk flask equipped with a stir bar. Into a 100 mL Schlenk flask equipped with a stir bar was charged 50 mmol (14.02 g) of the ligand of Example 1. To both flasks was added 100 mL of dry toluene. Both flasks were sealed with septa and allowed to stir. When the ligand was dissolved, the solution was transferred slowly via syringe into the vigorously stirring ZrCl$_4$ slurry. The pale yellow mixture was allowed to stir overnight in the dry box.

While the ligand/ZrCl$_4$ mixture was stirring, preparation of a Grignard solution was started. Two hundred mmol (200 mL) of benzylmagnesium chloride (1.0 M solution in diethyl ether) was charged via syringe to an oven-dried 500 mL Schlenk flask equipped with a stir bar and sealed with a septum. The ether was stripped under high vacuum (0.2 Torr). The vessel was taken into the dry box where 100 mL dry toluene was added to the residue. The residue was dissolved and removed from the dry box, placed on the high vacuum manifold, and stripped again. This procedure was repeated three additional times, until the residue was no longer a viscous reddish liquid, but an off-white powder.

When the powder stage was reached 100 mL of dry toluene was added and the solids dissolved. The vessel was removed from the dry box and placed under argon.

After stirring overnight, the ligand/ZrCl$_4$ mixture was bright yellow. The vessel was removed from the dry box and placed under argon beside the vessel containing the Grignard solution. The ligand/ZrCl$_4$ solution was covered with foil and chilled to −78° C. In the darkened room the Grignard solution was slowly transferred via double-ended cannula into the ligand/ZrCl$_4$ solution. The reaction mixture turned bright red when the addition was complete. The reaction was allowed to slowly warm to room temperature. After stirring for a few hours the vessel was returned to the dry box and filtered through a medium porosity frit. Toluene was added to the filtrate to adjust the volume to 500 mL. The filtrate was transferred to an amber bottle. A 1.0 mL subsample was removed and placed in a tared 10 mL flask. The subsample was vacuum stripped and the mass of the residue was used to determine the molarity of the solution at 0.089M.

Preparation of 1 liter of 0.02M solution was accomplished using 224.7 mL of catalyst solution and diluting to 1000 mL with dry toluene.

Example 4

A series of ethylene/hexene copolymers were made in a laboratory scale, slurry phase reactor using a catalyst composition comprising the catalyst precursor of Example 2 with modified methylaluminoxane, MMAO (7.0 wt % Al in heptane, commercially available from Akzo Chemicals, Inc.).

In each case, the catalyst composition was prepared by combining a solution of the catalyst precursor of Example 2 in benzene with the MMAO solution in the presence of 0.1 mL 1-hexene. Reaction conditions and results are shown in Table 1 below.

TABLE 1

| Example | Hexene mL | MMAO/Zr Mole Ratio | T,° C. | C$_2$ psi | Activity | BBF |
|---|---|---|---|---|---|---|
| 4a | 43 | 1000 | 65° C. | 85 | 115 K | 7.16 |
| 4b | 43 | 1000 | 75° C. | 85 | 80.6 K | 10.34 |
| 4c | 43 | 1000 | 85° C. | 85 | 49.1 K | 9.71 |
| 4d | 43 | 1000 | 65° C. | 170 | 101 K | 2.41 |
| 4e | 43 | 1000 | 92.9 K | 170 | 92.9 K | 4.95 |
| 4f | 43 | 1000 | 85° C. | 170 | 61.8 K | 2.37 |
| 4g | 21.5 | 1000 | 75° C. | 85 | 8.1 K | 3.16 |
| 4h | 43 | 1000 | 75° C. | 85 | 80.6 K | 10.34 |
| 4i | 86 | 1000 | 75° C. | 85 | 95.6 K | 17.99 |
| 4j | 43 | 2000 | 65° C. | 85 | 210 K | 7.30 |
| 4k | 43 | 1000 | 65° C. | 85 | 115 K | 7.16 |
| 4l | 43 | 500 | 65° C. | 85 | 4.6 K | 9.22 |

Example 5

A series of ethylene/hexene copolymers. were made in a laboratory scale, slurry phase reactor using catalyst compositions comprising various catalyst precursors according to the invention with MMAO cocatalyst.

In each case, the catalyst composition was prepared by contacting the ligand shown below in Table 2 with tetrabenzyl zirconium, dissolving the resulting material in toluene, and then contacting with MMAO solution (7.0 wt % Al in heptane, commercially available from Akzo Chemicals, Inc.) in the presence of 0.1 mL 1-hexene. Polymerization reactions were carried out at 65° C., 85 psi ethylene, 1.0 micromole Zr, and a MMAO/Zr mole ratio of 1,000. Ligands and results are shown in Table 2 below.

TABLE 2

| Example | Ligand | Activity | I21 | BBF |
|---|---|---|---|---|
| 5a | | 25647 | 9.83 | 10.51 |
| 5b | | 24,941 | 0.897 | 4.37 |

TABLE 2-continued

| Example | Ligand | Activity | I21 | BBF |
|---|---|---|---|---|
| 5c | | 5,647 | | |
| 5d | | 2,353 | | |
| 5e | | 23,294 | 0.511 | 9.23 |
| 5f | | 68,235 | too slow for measurement | 6.85 |
| 5g | | 10,118 | | 5.86 |

TABLE 2-continued

| Example | Ligand | Activity | I21 | BBF |
|---|---|---|---|---|
| 5h | [structure: 2-pyridyl-CH=N-(2,6-diisopropylphenyl)] | 39,059 | 1.04 | 12.49 |
| 5i | [structure: 2-pyridyl-CH2-NH-(2,6-diisopropylphenyl)] | 22,824 | 5.39 | 13.64 |
| 5j | [structure: 6-methyl-2-pyridyl-CH=N-(2,6-diisopropylphenyl)] | 15,765 | | 5.96 |
| 5k | [structure: 2-quinolyl-C(CH3)=N-(2,6-diisopropylphenyl)] | 40,941 | 2.42 | 13.36 |
| 5l | [structure: dihydropyridyl-C(CH3)2-NH-(2,6-diisopropylphenyl)] | 183,059 | too slow for measurement | 8.68 |

TABLE 2-continued

| Example | Ligand | Activity I21 | BBF |
|---|---|---|---|
| 5m | 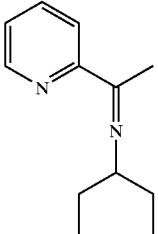 | 4706 | |
| 5n | 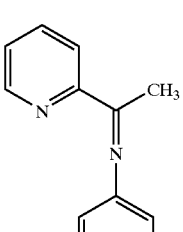 | 941 | |

Example 6

A series of ethylene/hexene copolymers were made in a laboratory scale, slurry phase reactor using mixed catalyst compositions according to the invention with MMAO cocatalyst.

In each case, the catalyst composition was prepared by contacting mixtures of the ligands shown below in Table 3 with tetrabenzyl zirconium, dissolving the resulting material in toluene, and then contacting with MMAO solution (7.0 wt % Al in heptane, commercially available from Akzo Chemicals, Inc.) in the presence of 0.1 mL 1-hexene. Polymerization reaction conditions were 65° C., 85 psi ethylene, 1.0 micromole Zr, and a MMAO/Zr mole ratio of 1,000. Ligands and results are shown in Table 3 below.

TABLE 3

| Example | Ligands | | Activity | BBF |
|---|---|---|---|---|
| 6a | 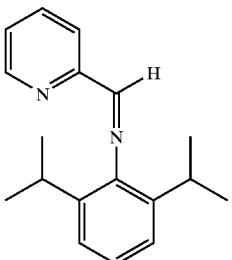 1 eq. | 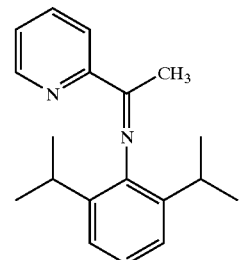 1 eq. | 46,588 | 8.64 |
| 6b | 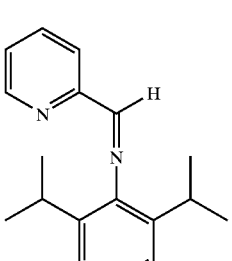 2 eq. | 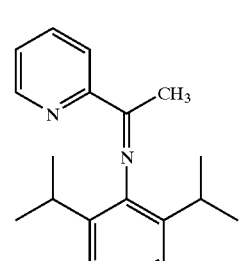 1 eq. | 109,176 | 7.90 |

Example 7

An ethylene/hexene copolymer was made in a laboratory scale, slurry phase reactor using a mixed catalyst composition comprising the catalyst precursor of Example 2, biscyclopentadienyl zirconium dichloride, and MMAO.

Polymerization reaction conditions were 65° C., 85 psi ethylene, 1.0 micromole Zr, and a MMAO/Zr mole ratio of 1,000. The activity of the catalyst composition was 20,706. Polyethylene copolymer having an I21 of 1.74 was made.

Example 8

The catalyst precursor of Example 3 combined with MMAO was used as the catalyst composition to polymerize an ethylene/1-hexene copolymer (density 0.917, melt index 1.0) in a pilot-scale, fluidized bed, gas phase reactor. The reactor was nominally 1 foot in diameter and was operated with a bed height of 8 feet and a superficial gas velocity of approximately 1.8 ft/sec. Total reactor pressure was 350 psig.

A seed bed was charged to the reactor and it was dried to <5 ppm water. The reactor was pressurized to 200 psig of ethylene. The 1-hexene/ethylene and hydrogen/ethylene mole ratio was established at 0.048 and 0.041. The bed temperature was adjusted to 70° C.

The catalyst composition was employed in liquid form. The catalyst composition was made by mixing the catalyst precursor of Example 3 in toluene with MMAO (2.8 wt % Al, commercially available from Akzo Chemicals, Inc.). Additional dilution of the catalyst composition was performed by adding isopentane to the mixture. The catalyst composition sprayed into the reactor with the aid of 5.0–7.0 lb/hr of nitrogen gas and a stream of 1950 lbs/hr of recycle gas.

Reactor static was clearly absent throughout the run. The expanded section, recycle line and distributor plate were free from fouling. The average particle size (APS) held steady and could be controlled by varying the nitrogen carrier flow and resin density.

Example 9

Preparation of [1-(2-Pyridyl)N-1-Methylethyl][1-N-2,6-Diisopropylphenyl]Amine

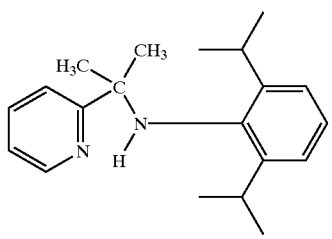

In a dry box, 22.45 mmol (6.34 g) 2-acetylpyridine(2,6-diisopropylphenylimine) were charged to a 250 mL round bottom flask equipped with a stir bar and septa. The flask was sealed, removed from the dry box and placed under nitrogen purge. Dry toluene (50 mL) was added and stirred to dissolve the ligand. The vessel was chilled to 0° C. in a wet ice bath. Trimethyl aluminum (Aldrich, 2.0 M in toluene) was added dropwise over ten minutes. The temperature of the reaction was not allowed to exceed 10° C. When addition of the trimethyl aluminum was complete, the mixture was allowed to warm slowly to room temperature, and then was then placed in an oil bath and heated to 400° C. for 25 minutes. The vessel was removed from the oil bath and placed in an ice bath. A dropping funnel containing 100 mL of 5% KOH was attached to the flask. The caustic was charged to the reaction dropwise over a 1 hour span. The mixture was transferred to a separatory funnel. The aqueous layer was removed. The solvent layer was washed with 100 mL water then 100 mL brine. The red-brown liquid product was dried over $Na_2SO_4$, vacuum stripped and placed under high vacuum over night.

80 mL of red-brown liquid was transferred to a 200 mL Schlenk flask equipped with a stir bar. A distillation head with a dry ice condenser was attached to the flask. The mixture was vacuum distilled yielding approximately 70 g of dark yellow viscous liquid product.

Example 10

A series of catalyst precursors according to the invention were made using the ligand of Example 9 and a variety of metal compounds. Each catalyst precursor was made by first combining the ligand in ether with methyllithium and then contacting the resulting product with the metal compound shown in Table 4 below. The resulting catalyst precursors were combined with a cocatalyst and used for the slurry homopolymerization of ethylene in a laboratory scale reactor in the manner described in Example 4.

The results are shown in Table 4.

TABLE 4

| Example | Metal Compound | Cocatalyst | g PE |
| --- | --- | --- | --- |
| 9a | $ZrCl_4$ | MMAO | 0.484 |
| 9b | $Cr(THF)_3Cl_3$ | MMAO | 0.239 |
| 9c | $V(THF)_3Cl_3$ | MMAO | 0.158 |
| 9d | $SmCl_3$ | MMAO | 0.797 |
| 9e | $YCl_3$ | MMAO | 0.935 |
| 9f | $TaCl_5$ | MMAO | 0.195 |
| 9g | $NbCl_5$ | MMAO | 0.185 |
| 9h | $SmCl_3$ | TIBA(100 eq) | 0.024 |
| 9i | $YCl_3$ | TIBA(100 eq) | 0.053 |
| 9j | $ZrCl_4$ | TIBA(100 eq) | 0.024 |
| 9k | $V(THF)_3Cl_3$ | TIBA(100 eq) | 0.022 |
| 9l | $Cr(THF)_3Cl_3$ | TIBA(100 eq) | 0.037 |
| 9m | NbCl5 | TIBA(100 eq) | 0.032 |
| 9n | TaCl5 | TIBA(100 eq) | 0.024 |
| 9o | $V(THF)_3Cl_3$ | DEAC(100 eq) | 0.090 |
| 9p | $Cr(THF)_3Cl_3$ | IBAO(100 eq) | 0.134 |

Example 11

Preparation of [1-(2-Pyridyl)N-1-Methylethyl][1-N-2,6-Diisopropylphenyl Amido]Zirconium Tribenzyl In a darkened room and darkened dry box, 5.0 mmol (1.45 g) of the ligand made in Example 10 were charged to a 100 mL Schlenk tube equipped with a stir bar. The ligand was dissolved in 5 mL of toluene. To a second vessel equipped with a stir bar was charged 5.5 mmol (2.5 g) tetrabenzyl zirconium and 10 mL toluene.

The ligand solution was transferred into the tetrabenzyl zirconium solution. The vessel was covered with foil and allowed to stir at room temperature in the dry box. After 6 hours at room temperature 80 mL dry hexane was added to the reaction solution and allowed to stir overnight. The reaction mixture was filtered through a medium porosity frit with approximately 2 g pale yellow solids collected.

Example 12

Preparation of [[1-(2-Pyridyl)N-1-Methylethyl]-[1-N-2,6-Diisopropylphenyl Amido]][2-Methyl-1-Phenyl-2-Propoxy]Zirconium Dibenzyl To an oven-dried, cooled, purged and sealed GC vial was charged 0.10 mL dried acetone. The GC vial was sealed in a shell vial and taken into the dry box. In a darkened room and darkened dry box 2.0 mmol (1.3 g) of the material made in Example 11 and 9 mL toluene were charged to 1100 mL Schlenk flask equipped with a stir bar. To a second GC vial was charged 2.0 mmol (146 uL) acetone and 1.0 mL toluene. The acetone/toluene solution was transferred dropwise via syringe into the stirred solution of [1-(2pyridyl) N-1-methylethyl][1-N-2,6-diisopropylphenylamido]zirconoum tribenzyl. The vessel was covered with foil and allowed to stir at room temperature in the dry box overnight.

The reaction solution was vacuum stripped to a tacky orange residue. Dry hexane (20 mL) was added and the residue stirred vigorously, then vacuum stripped again to a yellow-orange glass. Hexane was added again and vigorously stirred. The vessel was placed in a freezer (−24° C.) for approximately 2 hours. The mixture was filtered through a medium porosity frit. Pale yellow solids (0.8 g) were collected.

Example 13

Hexane (600 mL), triisobutylaluminum (100 μmoles of a 1.0M solution in toluene) and 1-hexene (43 mls, alumina dried) were charged to a 1 liter slurry reactor.

The complex from Example 11 (2.46 μmoles) and trityl (tetraperfluorophenyl)borate (2.33 μmoles) were weighed into an oven dried, glass vial. Toluene (1.0 ml) was added and the mixture was stirred for 5 minutes resulting in a yellow solution. Triisobutylaluminum (10 μmoles of a 1.0M solution in toluene) was added to the solution to make a reaction solution. An aliquot of the reaction solution (0.20 mls, 0.5 μmoles Zr) was charged to the reactor 4 minutes after the triisobutylaluminum addition and the reaction was started. The reactor was run at 75° C. and 85 psia ethylene pressure for 30 minutes.

The polyethylene resin produced weighed 76.5 g. The calculated activity was 360000 g/m mole Zr/100 psi ethylene/hour. The molecular weight of the resin was too high to obtain an I21 or I2.

Example 14

Hexane (600 mL), triisobutylaluminum (100 μmoles of a 1.0M solution in toluene) and 1-hexene (43 mls, alumina dried) were charged to a 1 liter slurry reactor.

Trityl(tetraperfluorophenyl)borate (1.89 μmoles, Akzo) was weighed into an oven dried, glass vial. Toluene (1.0 ml) was added resulting in a dark yellow solution. The complex described in Example 12, (2.0 μmoles, 0.025 mls of an 80 μmole/ml solution in deuterated benzene) was added to the dark yellow solution resulting in an immediate pale yellow solution. After 5 minutes of stirring tiisobutylaluminum (10 μmoles of a 1.0M solution in toluene) was added to the solution to make a reaction solution. An aliquot of the reaction solution (0.25 mls, 0.5 μmoles Zr) was charged to the reactor 2 minutes after the triisobutylaluminum addition the reaction was started. The reactor was operated at 75° C. and 85 psia ethylene pressure for 30 minutes. The product weighed 16.8 g. The activity was 79059 g/m mole Zr/100 psi ethylene/hour. The resin was treated with ~1000 ppm antioxidant (4 parts Irgafos®168, 1 part Irganox® 1076) & 3 g was loaded into a Tinius Olsen extrusion plastometer. The resin extruded through the plastometer under the weight of the plunger (100 g). I2 data was therefore not obtained, but the quick extrusion indicates a low molecular weight product. A 3 mil plaque was made of the treated resin which was analyzed on an FTIR giving a butyl branch frequency of 8.04/1000 $CH_2$.

Example 15

In each of Examples 15a–15f, in a darkened dry box and darkened room, 0.100 mmol of [1-(2-pyridyl)N-1-methylethyl][1-N-2,6-diisopropylphenylamido]zirconium tribenzyl was dissolved in 1.0 mL of benzene-$d_6$ in a 10 mL Schlenk flask. To a second vessel was charged 0.100 mmol of the desired reactant described in Table 5 and 0.5 mL benzene-$d_6$. The second solution was transferred into the first solution dropwise. The vessel was sealed, covered with foil and allowed to stir overnight. The resultant solutions were analyzed by 1H-nmr to determine the conversion of [1-(2-pyridyl)N-1-methylethyl][1-N-2,6-diisopropylphenylamido]zirconium tribenzyl to the products described in Table 5.

A series of ethylene/hexene copolymers were made in a laboratory scale, slurry phase reactor using products described in Table 5 with MMAO (7.0 wt % Al in heptane, commercially available from Akzo Chemicals, Inc.). In each case, the catalyst composition was prepared by combining a benzene solution of the product described in Table 5 with the MMAO solution in the presence of 0.1 mL 1-hexene. Reaction conditions were 85° C., 85 psi ethylene, 0.5 micro moles of zirconium complex, 43 mL 1-hexene, and 1000 equivalents of MMAO per zirconium. The results are shown in Table 5.

TABLE 5

| Example | Product | Reactant | Conversion | Activity | I21 |
|---------|---------|----------|------------|----------|-----|
| 15a | (structure) | Acetophenone | ~100% | 87,059 | too slow for measurement |

TABLE 5-continued

| Example | Product | Reactant | Conversion | Activity | I21 |
|---------|---------|----------|------------|----------|-----|
| 15b | | Benzaldehyde | ~100% | 101,647 | 0.235 |
| 15c | | Piperidine | ~83% | 96,941 | 0.141 |
| 15d | | Morpholine | ~94% | 148,235 | 0.292 |
| 15e | | Phenol | ~90% | 189,176 | too slow for measurement |

TABLE 5-continued

| Example | Product | Reactant | Conversion | Activity | I21 |
|---|---|---|---|---|---|
| 15f | (structure shown) | Acetylacetone | ~100% | 141,176 | 0.095 |

Example 16

Preparation of [1-(2-Pyridyl)-N-Ethenyl-(2,6-Diisopropylphenylamido)]Zirconium Tribenzyl In a dry box 10 mmol (2.80 g) 2-acetylpyridine(2,6-diisopropylphenylimine) was charged to 100 mL Schlenk flask equipped with a stir bar and sealed with a septa. The flask was removed from the dry box and placed under argon. Twenty mL tetrahydrofuran was added to the ligand and stirred to dissolve. The solution was chilled to −70° C. and 10 mmol (7.1 mL) methyl lithium (Aldrich, 1.4 M solution in ether) was added dropwise. The clear red-orange mixture was allowed to slowly warm to room temperature. The mixture thickened as it warmed. An additional 20 mL THF was added. After stirring at room temperature for 4 hours, the mixture was again chilled to −70° C. and 10 mmol (1.27 mL) chlorotrimethylsilane (Aldrich) was added dropwise to the ligand/methyllithium mixture. The red-orange mixture was allowed to slowly warm to room temperature and stir overnight.

The reaction mixture was vacuum stripped to a powdery, pale yellow residue which was taken into the dry box.

The resulting ligand was dissolved in 20 mL toluene. In a second flask 10 mmol (2.33 g) of zirconium (IV) chloride was slurried in 10 mL toluene. The ligand solution was added to the ZrCl$_4$ slurry with vigorous stirring. The yellow slurry was allowed to stir overnight in the dry box.

The slurry was removed from the dry box, vacuum stripped and 20 mL toluene added to the residue. In a second 100 mL Schlenk flask was charged 30 mmol (30 mL) benzylmagnesium chloride (Aldrich, 1.0 M solution in ether). The solution was vacuum stripped and the solvent replaced with toluene. Repeating the wash 3 times resulted in a powdery off-white residue which was dissolved in 20 ml toluene.

In a darkened lab and hood the benzylmagnesium chloride solution was cannula transferred into the chilled (−70° C.) ligand/ZrCl$_4$ slurry. The vessel was covered with foil and allow to slowly warm to room temperature and stir over night. The reaction mixture was taken into the dry box and filtered through a medium porosity frit. The solids were washed with toluene then discarded. The filtrate was transferred into an amber bottle.

Example 17

A series of ethylene/hexene copolymers were made in a laboratory scale, slurry phase reactor using a catalyst composition comprising the catalyst precursor of Example 17 with MMAO (7.0 wt % Al in heptane, commercially available from Akzo Chemicals, Inc.).

In each case, the catalyst composition was prepared by combining a solution of the catalyst precursor of Example 17 in benzene with the MMAO solution in the presence of 0.1 mL 1-hexene. Reaction conditions and results are shown in Table 6 below.

TABLE 6

| Example | C$_6$ mL | T, C | C$_2$ psi | gPE | Activity | I2 | MFR | Mn | PDI | BBF |
|---|---|---|---|---|---|---|---|---|---|---|
| 17a | 43 | 65 | 85 | 27.7 | 28,000 | .512 | 44.21 | 24,120 | 4.707 | 12.26 |
| 17b | 86 | 65 | 170 | 42.4 | 30,235 | NF | NF | — | — | 15.06 |
| 17c | 43 | 75 | 85 | 12.1 | 26,118 | .577 | 27.56 | 13,944 | 5.896 | 14.46 |
| 17d | 86 | 75 | 170 | 32.6 | 17,765 | .09 | 34.52 | 51,382 | 3.779 | 12.09 |
| 17e | 43 | 85 | 85 | 9.7 | 14,588 | 1.138 | 31.38 | 31,332 | 3.367 | 9.13 |
| 17f | 86 | 85 | 170 | 25.3 | 14,118 | .208 | 29.13 | 45,632 | 3.524 | 11.23 |

Example 18

Preparation of N-Tetrahydrofurfuryl[N-2,6-Diisopropylphenyl]Amine

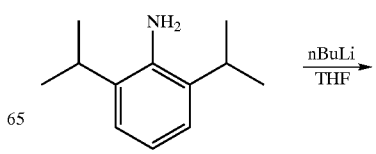

-continued

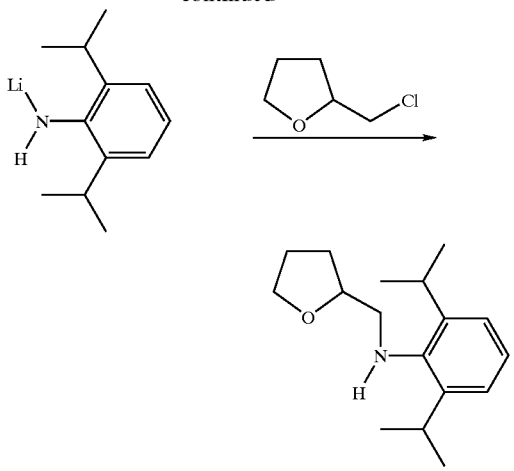

2,6-Diisopropyl aniline (50 mmol, 8.86 g Aldrich, 90%) was charged to an oven-dried, cooled Schlenk flask equipped with a stir bar and septa. The flask was placed under a nitrogen purge and 20 mL of dry tetrahydrofuran was added. The flask was chilled to 0° C. and n-butyl lithium (50 mmol, 17.8 mL, Aldrich, 2.81M solution in hexane) was added dropwise via syringe. The mixture was allowed to slowly warm to room temperature.

Tetrahydrofurfuryl chloride (50 mmol, 5.4 mL, Aldrich, 98%) was added via syringe and the mixture was heated at 50° C. overnight. The reaction solution was cooled to ambient temperature and hydrolyzed. The aqueous layer was extracted 3 times with ether. The organics were combined and vacuum stripped. The residue was vacuum distilled using a shortpath distillation column. The product distillate (140–144° C., 0.25 torr, 4 grams) was a clear yellow liquid.

Example 19

Preparation of [N-Tetrahydrofurfuryl][N-2.6-Diisopropylphenylamido]Zirconium Tribenzyl

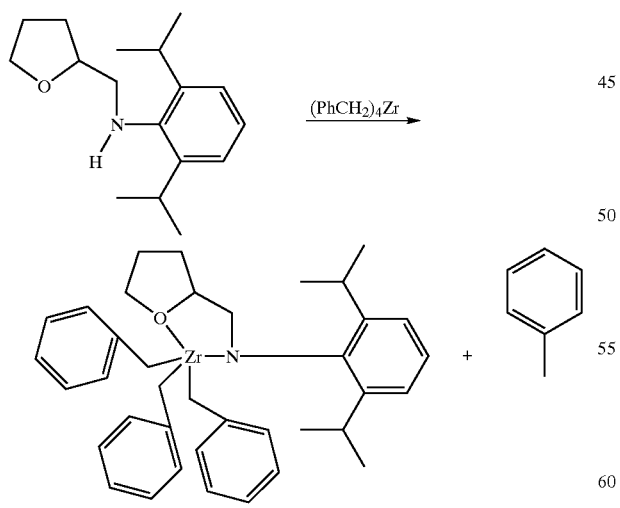

Tetrabenzyl zirconium (0.200 mmol, 0.091 g) was charged to a 7 mL amber bottle equipped with a stir bar and screw-cap. Dried benzene-$d_6$ (2 mL) was added and stirred to dissolve. To a second vial was charged the ligand made in Example 18 (0.200 mmol, 0.052 g,) and dried benzene-$d_6$ (1.0 mL). The N-tetrahydrofurfuryl][N-2,6-diisopropylphenylimine]solution was transferred into the stirred tetrabenzyl zirconium solution. The bottle was capped and the reaction solution was allowed to stir overnight.

Example 20

A series of ethylene/hexene copolymers were made in a laboratory scale, slurry phase reactor using a catalyst composition comprising the catalyst precursor of Example 19 with MMA (7.0 wt % Al in heptane, commercially available from Akzo Chemicals, Inc.).

In each case, the catalyst composition was prepared by combining a solution of the catalyst precursor in benzene with the MMAO solution in the presence of 0.1 mL 1-hexene. Polymerization reactions were carried out at 85 psi ethylene, 0.5 micromole Zr, and a MMAO/Zr mole ratio of 1,000. Reaction conditions and results are shown in Table 7 below.

TABLE 7

| Example | $C_6$ mL | T, C | $C_2$ psi | Activity | I21 | BBF |
|---|---|---|---|---|---|---|
| 20a | 43 | 65 | 85 | 35,765 | NF | 9.82 |
| 20b | 43 | 75 | 85 | 20,235 | .114 | 9.77 |
| 20c | 43 | 85 | 85 | 13,176 | — | — |

What is claimed is:

1. A catalyst composition comprising:

a) a catalyst precursor compound having the formula: $A_qML_n$ wherein each A has the formula:

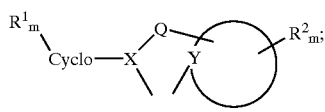

M is a Group 4 metal;

each L is a monovalent, bivalent, or trivalent anion;

Q is a bridging group containing one or more Group 13–16 atoms;

X and Y are each heteroatoms selected from the group consisting of N, O, S and P, said Y being contained in a heterocyclic ring additionally comprising from 2 to 7 carbon atoms, and substituted with from 0 to 5 $R^2$ groups, said Q being bonded to said heterocyclic ring at an atom other than Y;

Cyclo is a cyclic moiety;

each $R^1$ is independently a group containing 1 to 50 atoms selected from the group consisting of hydrogen and Group 13 to 17 elements, and two or more adjacent $R^1$ groups may be joined to form a cyclic moiety;

each $R^2$ is independently a group containing 1 to 50 atoms selected from the group consisting of hydrogen and Group 13 to 17 elements, and two or more adjacent $R^2$ groups may be joined to form a cyclic moiety;

each m is independently an integer from 0 to 5;

n is an integer from 1 to 4;

q is 1 or 2;

and when q is 2, the A groups are optionally connected by a bridging group Z containing one or more Group IIIA, group IVA, Group VA, or Group VIA elements; and b) an activating cocatalyst.

2. The catalyst composition of claim 1, wherein Cyclo is an aryl group.

3. The catalyst composition of claim 1, wherein X and Y are each nitrogen.

4. The catalyst composition of claim 3, wherein Y is contained in a pyridine ring.

5. The catalyst composition of claim 1, wherein Q is a substituted carbon wherein the substituents are each independently selected from the group consisting of alkyl, aryl, and heterocyclic ligand groups.

6. The catalyst composition of any one of claims 1–5, wherein $R^1$ independently each occurrence is an alkyl or aryl group.

7. The catalyst composition of claim 6, wherein $R^1$ each occurrence is an isopropyl group.

8. The catalyst composition of any one of claims 1–5, wherein at least one $R^1$ is ortho to X.

9. The catalyst composition of claim 6, wherein at least one $R^1$ is ortho to X.

10. The catalyst composition of claim 7, wherein at least one $R^1$ is ortho to X.

11. The catalyst composition of claim 6, wherein m is 2.

12. The catalyst composition of claim 7, wherein m is 2.

13. The catalyst composition of claim 8, wherein m is 2.

14. The catalyst composition of claim 9, wherein m is 2.

15. The catalyst composition of claim 11, wherein both $R^1$ groups are ortho to X.

16. The catalyst composition of claim 12, wherein both $R^1$ groups are ortho to X.

* * * * *